United States Patent

Yamazaki et al.

Patent Number: 5,440,036
Date of Patent: Aug. 8, 1995

[54] 1,4-BENZOXAZINE DERIVATIVES

[75] Inventors: Kazuo Yamazaki; Shigeru Adegawa, both of Narita; Yoichiro Ogawa, Chiba; Hideaki Matsuda, Abiko; Tadayuki Kuraishi, Narashino, all of Japan

[73] Assignee: SS Pharmaceutical Co., Ltd., Tokyo, Japan

[21] Appl. No.: 161,264

[22] Filed: Dec. 3, 1993

[30] Foreign Application Priority Data

Dec. 3, 1992 [JP] Japan ................... 4-324329
Apr. 22, 1993 [JP] Japan ................... 5-095925

[51] Int. Cl.⁶ .................................. C07D 265/36
[52] U.S. Cl. ................................... 544/105; 544/71
[58] Field of Search ............ 544/101, 102, 103, 104, 544/105, 71

[56] References Cited

FOREIGN PATENT DOCUMENTS

0289365A2  11/1988  European Pat. Off.
0432893A2   6/1991  European Pat. Off.
0441539A2   8/1991  European Pat. Off.

Primary Examiner—John M. Ford
Attorney, Agent, or Firm—Oblon, Spivak, McClelland, Maier & Neustadt

[57] ABSTRACT

A 1,4-benzoxazine derivative represented by the following formula (1):

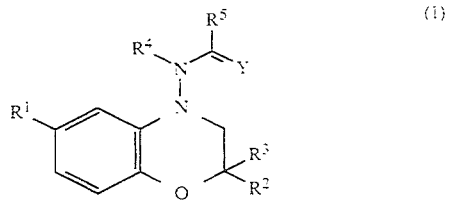

wherein $R^1$ represents an unsubstituted or halogen-substituted lower alkyl, unsubstituted or halogen-substituted lower alkylsulfonyl, nitro or cyano group, $R^2$ and $R^3$ may be the same or different and individually represent a hydrogen atom or a lower alkyl group or are fused together with the adjacent carbon atom into a 3- to 6-membered carbon ring, $R^4$ represents a hydrogen atom or an unsubstituted or substituted lower alkyl or acyl group, $R^5$ represents a hydrogen atom or a unsubstituted or substituted lower alkyl, lower alkenyl, lower alkoxyl, aryl, aryloxyl or heterocyclic ring group, and Y represents an oxygen or sulfur atom, with the proviso that $R^1$ is other than a nitro or cyano group when $R^2$ and $R^3$ are individually a methyl group, $R^4$ is a hydrogen atom, $R^5$ is a 3-chloropropyl group and Y is an oxygen atom; or a salt thereof.

15 Claims, No Drawings

1,4-BENZOXAZINE DERIVATIVES

BACKGROUND OF THE INVENTION

1) Field of the Invention

This invention relates to novel benzoxazine derivatives and salts thereof, which are useful as medicinal drugs, especially as preventives or therapeutics for circulatory diseases or bronchial diseases.

2) Description of the Related Art

As preventives or therapeutics for circulatory diseases led by ischemic heart diseases such as angina pectoris and myocardial infarction and including hypertension or bronchial diseases such as bronchial asthma, pharmaceuticals having smooth muscle relaxing effects, for example, direct smooth muscle relaxing agents, calcium antagonists, $\beta$-blockers, $\alpha$-blockers and the like have heretofore been used widely. However these pharmaceuticals are all accompanied by one or more drawbacks such as insufficient pharmacological effects and/or high side effects, leading to the outstanding desire for the development of more effective and safer therapeutics.

In the meantime, smooth muscle relaxing agents—which act in accordance with a new mechanism, that is, to activate the potassium channel in smooth muscle cells—have been developed in recent years. They have attracted interests as therapeutics for the abovementioned circulatory diseases or bronchial diseases. Known examples of compounds having such potassium channel activating effects include cromakalim [($\pm$)-trans-6-cyano-2,2-dimethyl-4-(2-oxopyrrolidin-1-yl)-3,4-dihydro-2H-1-benzopyran-3-ol].

These potassium channel activating agents are however still not considered to be fully satisfactory medicinal drugs when they are evaluated in view of both aspects of effectiveness and safety. It has therefore been desired to develop potassium channel activating agents which are still safer and more effective.

SUMMARY OF THE INVENTION

The present inventors have therefore synthesized a variety of compounds and screened them relying upon their potassium channel activating effects as an index. As a result, it has been found that novel benzoxazine derivatives represented by the below-described formula (1) and their salts have strong potassium channel activating effects and are useful as medicinal drugs, leading to the completion of the present invention.

In one aspect of the present invention, there is thus provided a 1,4-benzoxazine derivative represented by the following formula (1):

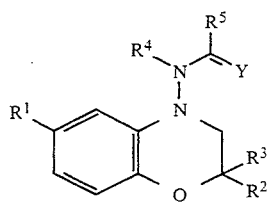

wherein $R^1$ represents an unsubstituted or halogen-substituted lower alkyl, unsubstituted or halogen-substituted lower alkylsulfonyl, nitro or cyano group, $R^2$ and $R^3$ may be the same or different and individually represent a hydrogen atom or a lower alkyl group or are fused together with the adjacent carbon atom into a 3- to 6-membered carbon ring, $R^4$ represents a hydrogen atom or an unsubstituted or substituted lower alkyl or acyl group, $R^5$ represents a hydrogen atom or a unsubstituted or substituted lower alkyl, lower alkenyl, lower alkoxyl, aryl, aryloxyl or heterocyclic ring group, and Y represents an oxygen or sulfur atom, with the proviso that $R^1$ is other than a nitro or cyano group when $R^2$ and $R^3$ are individually a methyl group, $R^4$ is a hydrogen atom, $R^5$ is a 3-chloropropyl group and Y is an oxygen atom; or a salt thereof.

The compounds according to the present invention have potassium channel activating effects and are useful as preventives or therapeutics for circulatory diseases, led by ischemic heart diseases such as angina pectoris and myocardial infarction and including hypertension and arrhythmia. They are also useful as therapeutics for various problems associated with contraction of smooth muscle such as bronchial problems or genital problems.

DETAILED DESCRIPTION OF THE INVENTION AND PREFERRED EMBODIMENTS

In the compound (1) according to the present invention, the lower alkyl group can be a straight or branched alkyl group having 1–6 carbon atoms, specifically a methyl, ethyl, n-propyl, isopropyl, n-butyl, n-pentyl or n-hexyl group. Examples of the 3- to 6-membered carbon ring include cyclopropane, cyclopentane and cyclohexane rings.

The acyl group can be an acetyl, propionyl or butyryl group. The lower alkenyl group can be a straight or branched alkenyl group having 2–6 carbon atoms, specifically a vinyl, allyl, 2-propenyl or 3-butenyl group. The lower alkoxy group can be a methoxy, ethoxy, propoxy or butoxy group. The aryl group can be a phenyl or naphthyl group. Illustrative of the heterocyclic group include pyrrolyl, oxazyl, imidazolyl, pyridyl, pyrimidyl, furanyl and thienyl groups.

Examples of the halogen atom include fluorine, chlorine, bromine and iodine atoms. Illustrative substituents which are usable in relation to the above expression "substituted" include halogen atoms, hydroxy group, alkoxy groups having 1–6 carbon atoms, aryloxy groups, aralkyloxy groups, nitroxy groups, amino group, cyano group, nitro group, alkylamino groups having 1–6 carbon atoms, dialkylamino groups having 2–12 carbon atoms, cycloamino groups, aryl groups, aminosulfonyl group, and alkyl groups having 1–6 carbon atoms (as substituents to aryl groups or heterocyclic groups). One to several of these substituents can be introduced.

Illustrative of the salt of the 1,4-benzoxazine derivative (1) include inorganic acid salts such as the hydrochloride, nitrate, sulfate and hydrobromide; and organic acid salts such as the lactate, malonate, fumarate, maleate, tartrate, citrate and acetate.

Each compound (1) or its salt, which pertains to the present invention, can be prepared, for example, in accordance with the following reaction scheme:

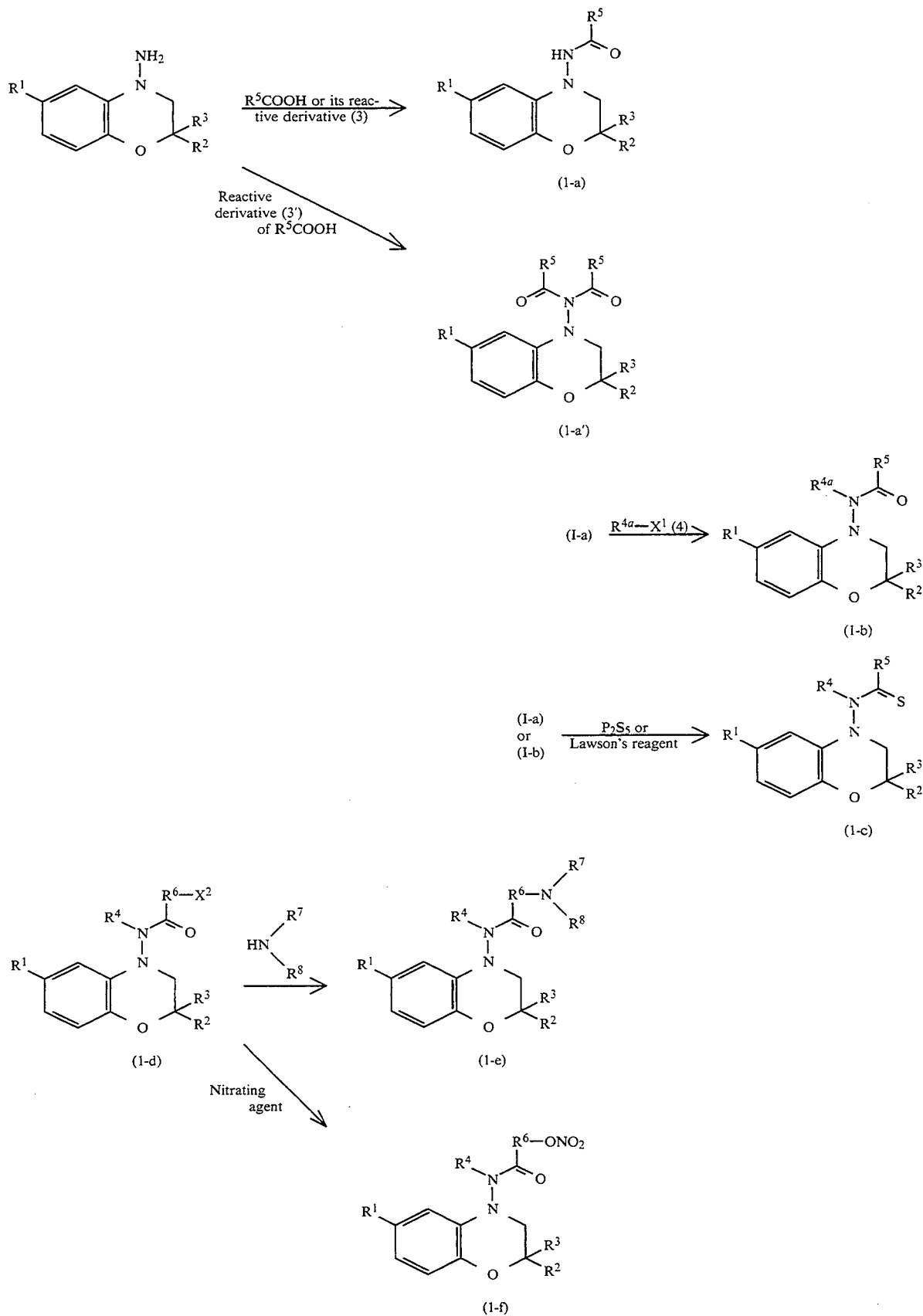
wherein $R^{4a}$ represents an unsubstituted or substituted lower alkyl group, $R^6$ represents a lower alkylene Namely, the compound (1-a) is prepared by reacting the carboxylic acid or its reactive derivative (3) with the N-amino-1,4-benzoxazine (2). The compound (1-a') is prepared by reacting the reactive derivative (3') of the carboxylic acid. The compound (1-b) is prepared by reacting the unsubstituted or substituted lower alkyl halide (4) with the compound (1-a). Further, the compound (1-c) in which Y stands for a sulfur atom is prepared by reacting a sulfurizing agent such as phosphorus pentasulfide or the Lowson's reagent with the compound (1-a) or (1-b).

Reaction of an amine (alkylamine, dialkylamine, cyclic amine or the like) with the compound (1-d) provides the compound (1-e). Further, reaction of a nitrating agent with the compound (1-d) furnishes the compound (1-f).

The N-amino-1,4-benzoxazine (2) as the raw material can be prepared, for example, in accordance with the process disclosed in Japanese Patent Application Laid-Open No. HEI 4-178375.

Examples of the reactive derivative (3) of the carboxylic acid include esters such as the methyl ester and the ethyl ester; acid halides such as the acid chloride; acid anhydrides; and mixed acid anhydrides with alkyl carbonates or the like.

The reaction between the N-amino-1,4-benzoxazine (2) and the carboxylic acid or its reactive derivative (3) may preferably be carried out at 0° C. to a refluxing temperature for one to several hours. When the carboxylic acid (3) is reacted in the free form, it is preferred to conduct the reaction in the presence of a condensing agent such as dicyclohexylcarbodiimide although they may be reacted directly without such a condensing agent. The reaction may be conducted without any reaction solvent, but methylene chloride, chloroform, ethyl ether, tetrahydrofuran, dioxane, dimethylformamide, pyridine, benzene, toluene, xylene, ethyl acetate, acetonitrile or the like can be used. It is preferred to conduct the reaction in the presence of a base. Examples of such a base include organic bases such as triethylamine, pyridine and dimethylaniline; and inorganic bases such as sodium bicarbonate, potassium carbonate, sodium carbonate, potassium hydroxide and sodium hydroxide.

The reaction between the compound (2) and the reactive derivative (3') of the carboxylic acid may preferably be conducted at room temperature to a refluxing temperature for 1 to 40 hours. Although the reaction can be conducted without any reaction solvent, pyridine or the like can be used. It is preferable to conducted the reaction in the presence of a base. Usable examples of the base include 4-dimethylaminopyridine.

Illustrative of the reactive derivative (3') of the carboxylic acid include acid halides, such as the acid chloride, and acid anhydrides.

The reaction between the compound (1-a) and the unsubstituted or substituted lower alkyl halide (4) can be carried out, for example, by stirring them in a solvent in the presence of a base at 0° C. to room temperature for 0.1 to several hours. Usable examples of the solvent include ethyl ether, tetrahydrofuran, dioxane, benzene, toluene, xylene and dimethylformamide or the like. On the other hand, usable examples of the base include sodium hydride, sodium alcoholates and sodium amides or the like.

The reaction between the compound (1-a) or compound (1-b) and the sulfurizing agent can be conducted using phosphorus pentasulfide, the Lawson's reagent or the like while heating them in a solvent for 0.5 to several hours. Usable examples of the solvent include benzene, toluene and xylene.

The reaction between the compound (1-d) and the amine can be conducted by stirring them for 1 hour or so in a solvent such as a lower alcohol.

The reaction between the compound (1-d) and/the nitrating agent can be carried out by stirring them at 0° C. to a refluxing temperature for 1–60 hours in a solvent such as acetonitrile. Usable examples of the nitrating agent include silver nitrate.

To isolate the target compounds from the reaction mixtures in these reactions, washing, extraction, recrystallization, silica gel column chromatography and the like can be used either singly or in combination.

Certain compounds (I) of the present invention, which were obtained as described above, were tested for their pharmacological effects. The test and its results will be summarized next.

Vasorelaxing effect to endothelium-ablated preparations of the rat aorta:

The aorta of each rat (body weight: 200 to 330 g) was isolated and cut at a width of about 3 mm. Endothelium was then ablated off to form a ring preparation. That preparation was incubated at 37° C., and then suspended under a load of 2 g in 10 ml of the Krebs-Henseleit solution which had been aerated with a mixed gas (95% $O_2$, 5% $CO_2$). Tension was isometrically recorded via an FD transducer ("T2-30-240", trade name; manufactured by Orientec) and a dynamic strain gauge ("6M81", trade name; manufactured by NEC-San-ei) Upon an elapsed time of 60 minutes or longer subsequent to the suspension, that is, after the preparation had become stable, $10^{-7}$M noradrenaline (Nor) was applied several times. Under contraction by $10^{-7}$M Nor, $10^{-7}$ acetylcholine was applied. Preparations which were not relaxed by the application of $10^{-7}$ acetylcholine were used in the experiment. 30 mM $K^+$ were applied. From the time point that its contraction had became uniform, a sample compound was cumulatively applied at intervals of 10 minutes so that the 50% inhibition concentration ($IC_{50}$) was calculated. The results are presented in Table 1.

| Compound No. | $IC_{50}$ ($\times 10^{-8}$ M) |
| --- | --- |
| 8 | 1.26 |
| 11 | 2.88 |
| 20 | 5.14 |
| 24 | 3.79 |
| 27 | 3.36 |
| 56 | 0.96 |
| 57 | 1.52 |
| 58 | 1.43 |
| Cromakalim | 13.4 |

As is apparent from the above results, the compounds according to the present invention have been found to have superior effects to cromakalim.

The present invention will hereinafter be described in detail by the following Referential Examples and Examples. It is however to be borne in mind that the present invention will not be limited whatsoever by them.

REFERENTIAL EXAMPLE 1

3,4-Dihydro-6-trifluoromethyl-2H-1,4-benzoxazine-2-spiro-cyclopropane

Under ice cooling, 1.1 ml of a 1M solution of diborane in tetrahydrofuran were added dropwise to a solution of 1.07 g of 3,4-dihydro-6-trifluoromethyl-3-oxo-2H-1,4-benzoxazine-2-spiro-cyclopropane in tetrahydrofuran, followed by stirring at room temperature for 4 hours. The reaction mixture was ice cooled, to which iced water was added, followed by stirring at room temperature for 15 minutes. The reaction mixture was extracted with ethyl ether and the extract was dried over magnesium sulfate. The ethyl ether was distilled off and the residue was purified by chromatography on a silica gel column, whereby 0.96 g of the title compound was obtained (yield: 95%).

Appearance: Oil $IR\nu_{max}^{KBr}cm^{-1}$: 3406, 1493, 1342. $^1$H-NMR (CDCl$_3$) δ: 0.58–0.85(m,2H), 0.90–1.17(m,2H), 3.31(s,2H), 3.66(br,1H), 6.64–7.00(m,3H).

In a similar manner, the following compounds were obtained:

6-Cyano-3,4-dihydro-2H-1,4-benzoxazine-2-spiro-cyclopropane

Appearance: Colorless crystals m.p.: 93°–94° C. $IR\nu_{max}^{KBr}cm^{-1}$: 2222, 1497, 1300. $^1$H-NMR (CDCl$_3$) δ0.58–0.84(m,2H), 0.90–1.16(m,2H), 3.33(s,2H), 3.72(br,1H), 6.71(d,J=8 Hz,1H), 6.86–7.00(m,2H).

3,4-Dihydro-2,2-dimethyl-6-(pentafluoroethyl)sulfonyl-2H-1,4-benzoxazine

Appearance: Colorless prisms m.p.: 100°–102° C. (ether) $IR\nu_{max}^{KBr}cm^{-1}$: 1514, 1360. $^1$H-NMR (CDCl$_3$) δ: 1.37(s,6H), 3.15(s,2H), 4.00(br,1H), 6.92(d,J=9 Hz,1H), 7.20(d,J=3 Hz,1H), 7.33(dd,J=3,9 Hz,1H).

3,4-Dihydro-2,2-dimethyl-6-(nonafluorobutyl)sulfonyl-2H-1,4-benzoxazine

Appearance: Colorless prisms m.p.: 105°–106° C. $IR\nu_{max}^{KBr}cm^{-1}$: 1516, 1360. $^1$H-NMR (CDCl$_3$) δ7.12–7.42(m,2H), 6.91(d,J=9 Hz,1H), 3.70(br,2H), 3.15(s,2H), 1.37(s,6H).

3,4-Dihydro-2,2-diethyl-6-trifluoromethyl-2H-1,4-benzoxazine

Appearance: Oil $IR\nu_{max}^{KBr}cm^{-1}$: 1494. $^1$H-NMR (CDCl$_3$) δ: 0.92(t,J=8 Hz,6H), 1.60(m,4H), 3.12(s,2H), 3.30–3.90(br,1H), 6.75–7.00(m,3H).

REFERENTIAL Example 2

4-Amino-3,4-dihydro-6-trifluoromethyl-2H-1,4-benzoxazine-2-spiro-cyclopropane 3,4-Dihydro-6-trifluoromethyl-2H-1,4-benzoxazine-2-spiro-cyclopropane (930 mg) was dissolved in 0.6 ml of acetic acid and 10 ml of methanol. Added dropwise to the resulting solution was a solution of 616 mg of sodium nitrite in 2 ml of water. The reaction mixture was stirred for 3 hours at room temperature, poured into water and then extracted with chloroform. The organic layer was washed with saturate saline and then dried over anhydrous magnesium sulfate. The chloroform was distilled off and the residue was dissolved in 1.1 ml of acetic acid and 12 ml of ethanol. Zinc powder (1.13 g) was added little by little, followed by stirring for 2 hours at room temperature. Insoluble substance was filtered off and the filtrate was concentrated. The residue was dissolved in chloroform. The solution so formed was successively washed with a 10% aqueous solution of sodium hydroxide, water and saturated brine and then dried over anhydrous magnesium sulfate. The solvent was distilled off and the residue was purified by silica gel chromatography, whereby 707 mg of the title compound were obtained (yield 71%).

Appearance: Colorless crystals m.p.: 38°–39° C. $IR\nu_{max}^{KBr}cm^{-1}$: 3344, 1509, 1313. $^1$H-NMR (CDCl$_3$) δ: 0.63–0.87 (m,2H), 0.94–1.18(m,2H), 3.33(s,2H), 3.60(br,2H), 6.73 (d,J=8 Hz, 1H), 6.98(dd,J=8,2 Hz,1H), 7.47(d,J=2 Hz,1H).

In a similar manner, the following compounds were obtained:

4-Amino-6-cyano-3,4-dihydro-2H-1,4-benzoxazine-2-spiro-cyclopropane

Appearance: Colorless crystals m.p.: 144°–145° C. $IR\nu_{max}^{KBr}cm^{-1}$: 2222, 1500, 1291. $^1$H-NMR (CDCl$_3$) δ: 0.64–0.88(m,2H), 0.94–1.18(m,2H), 3.32(s,2H), 3.54(br,2H), 6.69(d,J=8 Hz,1H), 7.01(dd,J=8,2 Hz,1H), 7.50(d,J=2 Hz,1H).

4-Amino-3,4-dihydro-2,2-dimethyl-6-(pentafluoroethyl)sulfonyl-2H-1,4-benzoxazine Appearance: Colorless prisms m.p.: 105°–106° C. $IR\nu_{max}^{KBr}cm^{-1}$: 1501, 1349. $^1$H-NMR (CDCl$_3$) δ: 1.40(s,6H), 3.24(s,2H), 4.24(br,2H), 6.93(d,J=9 Hz,1H), 4.24(br,2H), 7.42(dd,J=3,9 Hz,1H), 7.85(d,J=3 Hz,1H).

4-Amino-3,4-dihydro-2,2-dimethyl-6-(nonafluorobutyl)sulfonyl-2H-1,4-benzoxazine

Appearance: Colorless prisms m.p: 105°–106° C. $IR\nu_{max}^{KBr}cm^{-1}$: 1501, 1350. $^1$H-NMR (CDCl$_3$) δ: 1.41(s,6H), 3.20(s,2H), 3.50(br,2H), 6.91(d,J=9 Hz,1H), 7.40(dd,J=3,9 Hz,1H), 7.82(d,J=3 Hz,1H).

4-Amino-3,4-dihydro-2,2-diethyl-6-trifluoromethyl-2H-1,4-benzoxazine

Appearance: Colorless crystals m.p.: 64°–66° C. $IR\nu_{max}^{KBr}cm^{-1}$: 1506, 1321. $^1$H-NMR (CDCl$_3$) δ: 0.92(t,J=8 Hz,6H), 1.54–1.84(m,4H), 3.14(s,2H), 3.24–3.80 (br,2H), 6.79(d,J=8 Hz,1H), 7.00(dd,J=8,2 Hz, 1H), 7.39(d,J=2 Hz, 1H).

EXAMPLE 1

4-Acetylamino-2,2-dimethyl-6-trifluoromethyl-1,4-benzoxazine (Compound No. 2)

Acetic acid (3 ml) was added to 123 mg of 4-amino-2,2-dimethyl-6-trifluoromethyl-1,4-benzoxazine, followed by refluxing for 1 hour. The acetic acid was distilled off under reduced pressure and the residue was dissolved in ethyl acetate. The resulting solution was washed first with a 1N aqueous solution of sodium hydroxide and then with water, and was dried over magnesium sulfate. The solvent was distilled off under reduced pressure and the residue was purified by chromatography on a silica gel column, whereby 90 mg of Compound No. 2 were obtained (yield: 63%).

EXAMPLE 2

2,2-Dimethyl-4-trifluoroacetylamino-6-trifluoromethyl-1,4-benzoxazine (Compound No. 4)

4-Amino-2,2-dimethyl-6-trifluoromethyl-1,4-benzoxazine (123 mg) was dissolved in 1.5 ml of pyridine, followed by the dropwise addition of 0.085 ml of trifluoroacetic anhydride under ice cooling. The reaction mixture so obtained was stirred for 1.5 hours at room temperature. Iced water was added, followed by extraction with ethyl ether. The ethyl ether layer was washed with water and then dried over magnesium sulfate. The ethyl ether was distilled off and the residue was purified by chromatography on a silica gel column, whereby 157 mg of Compound No. 4 were obtained (yield: 92%).

EXAMPLE 3

4-Benzoylamino-2,2-dimethyl-6-trifluoromethyl-1,4-benzoxazine (Compound No. 5)

4-Amino-2,2-dimethyl-6-trifluoromethyl-1,4-benzoxazine (123 mg) and triethylamine (0.085 ml) were dissolved in 2 ml of methylene chloride, followed by the dropwise addition of 0.07 ml of benzoyl chloride under ice cooling. The reaction mixture so obtained was stirred for 3 hours at room temperature. Iced water was added, followed by extraction with methylene chloride. The methylene chloride layer was washed with water and dried over magnesium sulfate. The solvent was distilled off and the residue was purified by chromatography on a silica gel column, whereby 161 mg of Compound No. 5 were obtained (yield: 92%).

EXAMPLE 4

2,2-Dimethyl-6-nitro-4-(N-propanoyl-N-methyl)amino-1,4-benzoxazine (Compound No. 17)

2,2-Dimethyl-6-nitro-4-propanoylamino-1,4-benzoxazine (Compound No. 8; 368 mg) was dissolved in 3 ml of dimethylformamide. Under ice cooling, 63 mg of 60% sodium hydride were added, followed by stirring for 5 minutes. Methyl iodide (0.2 ml) was next added, followed by stirring for 15 minutes. The reaction mixture was added with iced water and then extracted with ethyl ether. The extract was washed with water and then dried over magnesium sulfate. The solvent was distilled off under reduced pressure and the residue was purified by chromatography on a silica gel column, whereby 215 mg of Compound No. 17 were obtained (yield: 56%).

EXAMPLE 5

2,2-Dimethyl-4-thiopropanoylamino-6-trifluoromethyl-1,4-benzoxazine (Compound No. 18)

2,2-Dimethyl-4-propanoylamino-6-trifluoromethyl-1,4-benzoxazine (Compound No. 3; 282 mg) and the Lawson's reagent (377 mg) were suspended in 5 ml of toluene, followed by refluxing for 1 hour under a nitrogen atmosphere. After the reaction mixture was allowed to gradually cool down, precipitated crystals were filtered off and the filtrate was concentrated under reduced pressure. The residue was purified by chromatography on an alumina column, followed by recrystallization from chloroform-hexane. Compound No. 18 was hence obtained in an amount of 180 mg (yield: 60%).

EXAMPLE 6

3,4-Dihydro-6-cyano-2,2-dimethyl-4-[2-(dimethylamino)acetyl]amino-2H-1,4-benzoxazine (Compound No. 44)

3,4-Dihydro-6-cyano-2,2-dimethyl-4-(chloroacetyl)amino-2H-1,4-benzoxazine (Compound No. 15; 0.124 g) was dissolved in 5 ml of methanol, followed by the addition of 0.2 g of a 50% aqueous solution of dimethylamine at 0° C. under stirring. After the reaction mixture was stirred for 1 hour at room temperature, the solvent was distilled off. The residue was purified by chromatography on a silica gel column and then recrystallized from ethyl ether, whereby 19.9 mg of Compound No. 44 were obtained in the form of colorless needles (yield: 15.6%).

EXAMPLE 7

3,4-Dihydro-2,2-dimethyl-6-(nonafluorobutyl)sulfonyl-4-(methoxycarbonyl)amino-2H-1,4-benzoxazine (Compound No. 53)

3,4-Dihydro-4-amino-2,2-dimethyl-6-(nonafluorobutyl)sulfonyl-2H-1,4-benzoxazine (0.46 g) was dissolved in 5 ml of pyridine, followed by the dropwise addition of 0.12 ml of methyl chloroformate under ice cooling and stirring. After the reaction mixture was stirred for 15 hours at room temperature, the reaction mixture was added with 10% hydrochloric acid and then extracted twice with chloroform. The combined chloroform layer was washed with water and with saturated brine and was then dried over magnesium sulfate. The solvent was distilled off and the residue was purified by chromatography on a silica gel column, whereby 0.77 g of Compound No. 53 was obtained (yield: 70 %).

EXAMPLE 8

6-Cyano-4-diacetylamino-3,4-dihydro-2H-1,4-benzoxazine-2-spiro-cyclopropane (Compound No. 38)

4-Amino-6-cyano-3,4-dihydro-2H-1,4-benzoxazine-2-spiro-cyclopropane (0.201 g), acetic anhydride (0.14 ml) and 4-dimethylaminopyridine (0.01 g) were dissolved in 3 ml of pyridine, followed by stirring for 24 hours at room temperature. The reaction mixture was added with chloroform, washed first with dilute hydrochloric acid and then with water, and dried over anhydrous magnesium sulfate. The solvent was distilled off and the residue was purified by chromatography on a silica gel column, whereby 100 mg of Compound 38 were obtained (yield: 35%).

EXAMPLE 9

3,4-Dihydro-6-nitro-2,2-dimethyl-4-[2-(nitroxy)acetyl]amino-2H-1,4-benzoxazine (Compound No. 23)

3,4-Dihydro-6-nitro-2,2-dimethyl-4-(bromoacetyl)amino-2H-1,4-benzoxazine (Compound No. 22; 0.258 g) was dissolved in 3 ml of acetonitrile, to which 0.255 g of silver nitrate was added, followed by stirring for 48 hours at room temperature. The solvent was distilled off. The residue was purified by chromatography on a silica gel column and then recrystallized from ethyl ether, whereby 0.08 g of Compound 23 was obtained in the form of colorless crystals (yield: 33%).

EXAMPLE 10

In a manner similar to Examples 1 to 9, the compounds presented in Tables 1 to 19 were obtained. Tables 1 to 19 also show physical properties of the compounds obtained in Examples 1 to 9.

TABLE 1

| Comp'd No. | Structural formula | m.p. (°C.) | IR (cm$^{-1}$) | NMR δ ppm (CDCl$_3$) |
| --- | --- | --- | --- | --- |
| 1 | F$_3$C-[benzoxazine with NHCHO] | 135–137 | 3235, 1678 | 1.44, 1.47(sX2, 6H), 3.26, 3.38(sX2, 2H), 6.80–7.55(m, 3H), 8.35(m, 1H). |

TABLE 1-continued

| Comp'd No. | Structural formula | m.p. (°C.) | IR (cm⁻¹) | NMR δ ppm (CDCl₃) |
|---|---|---|---|---|
| 2 | F₃C—[benzene ring]—N(NHCOCH₃)—CH₂—C(CH₃)₂—O (morpholine-type ring) | 137–138 | 3250<br>1675 | 1.36–1.45(m, 6H),<br>2.01, 2.10(sX2, 3H),<br>3.18, 3.30(sX2, 2H),<br>6.70–7.90(m, 4H). |
| 3 | F₃C—[benzene ring]—N(NHCOC₂H₅)—ring | 132–133 | 3245<br>1671 | 1.13, 1.17(tX2, J=8Hz, 3H),<br>1.40(m, 6H),<br>2.22, 2.42(qX2, J=8Hz, 2H),<br>3.16, 3.29(sX2, 2H),<br>6.70–7.90(m, 4H). |
| 4 | F₃C—[benzene ring]—N(NHCOCF₃)—ring | 141–142 | 3224<br>1725 | 1.39(s, 6H), 3.29(s, 2H),<br>6.72–7.23(m, 3H),<br>8.34(s, 1H). |

TABLE 2

| Comp'd No. | Structural formula | m.p. (°C.) | IR (cm⁻¹) | NMR δ ppm (CDCl₃) |
|---|---|---|---|---|
| 5 | F₃C—[benzene ring]—N(NHCO—C₆H₅)—ring | 160–162 | 3227<br>1661 | 1.35(s, 6H), 2.33(s, 2H),<br>6.70–7.90(m, 8H),<br>9.50(s, 1H). |
| 6 | F₃C—[benzene ring]—N(NHCH—[benzene ring with Cl and SO₂NH₂])—ring | 263–265 | 1654<br>1338<br>1163 | 1.46(s, 6H), 3.44(s, 2H)<br>6.80–7.10(m, 3H),<br>7.62(d, J=8Hz, 1H),<br>8.07(dd, J=8.2Hz, 1H),<br>8.63(d, J=2Hz, 1H). |
| 7 | O₂N—[benzene ring]—N(NHCOCH₃)—ring | 138–140 | 1675<br>1522<br>1338 | 1.40, 1.47(sX2, 6H),<br>2.08, 2.12(sX2, 3H),<br>3.27, 3.38(sX2, 2H),<br>6.80(m, 1H),<br>7.50–8.00(m, 3H). |
| 8 | O₂N—[benzene ring]—N(NHCOC₂H₅)—ring | 161–163 | 1670<br>1516<br>1336 | 1.00–1.55(m, 9H),<br>2.15–2.60(m, 2H),<br>3.24, 3.40(sX2, 2H),<br>6.70–6.90(m, 1H),<br>7.50–7.85(m, 3H). |

TABLE 3

| Comp'd No. | Structural formula | m.p. (°C.) | IR (cm⁻¹) | NMR δ ppm (CDCl₃) |
|---|---|---|---|---|
| 9 | O₂N—[benzene ring]—N(NHCOC₃H₇)—ring | 125–126 | 1670<br>1522<br>1339 | 0.80–1.95(m, 11H),<br>2.05–2.50(m, 2H),<br>3.24, 3.40(sX2, 2H),<br>6.70–6.90(m, 1H),<br>7.50–7.90(m, 3H). |

TABLE 3-continued

| Comp'd No. | Structural formula | m.p. (°C.) | IR (cm⁻¹) | NMR δ ppm (CDCl₃) |
|---|---|---|---|---|
| 10 | O₂N-[benzene]-N(NHCO-iPr)-CH₂-C(CH₃)₂-O | 192-193 | 1672, 1518, 1337 | 1.05-1.60(m, 12H), 2.50(m, 1H), 3.22, 3.36(sX2, 2H), 6.78(m, 1H), 7.50-7.85(m, 3H). |
| 11 | O₂N-[benzene]-N(NHCO-cyclopropyl)-CH₂-C(CH₃)₂-O | 148-149 | 1670, 1512, 1339 | 1.42(m, 6H), 3.25, 3.40(sX2, 2H), 5.72-7.00(m, 4H), 7.50-8.05(m, 3H). |
| 12 | NC-[benzene]-N(NHCOCH₃)-CH₂-C(CH₃)₂-O | 144-146 | 2223, 1671 | 1.39, 1.46(sX2, 6H), 2.07, 2.11(sX2, 3H), 3.23, 3.36(sX2, 2H), 6.72-7.80(m, 4H). |

TABLE 4

| Comp'd No. | Structural formula | m.p. (°C.) | IR (cm⁻¹) | NMR δ ppm (CDCl₃) |
|---|---|---|---|---|
| 13 | NC-[benzene]-N(NHCOC₂H₅)-CH₂-C(CH₃)₂-O | 150-152 | 2220, 1670 | 1.04-1.50(m, 9H), 2.16-2.50(m, 2H), 3.20, 3.34(sX2, 2H), 6.73-7.20(m, 4H). |
| 14 | NC-[benzene]-N(NHCO-3-pyridyl)-CH₂-C(CH₃)₂-O | 211-212 | 2224, 1662 | 1.42(s, 6H), 3.47(s, 2H), 6.82(d, J=8Hz, 1H), 6.90-7.10(m, 2H), 7.46(m, 1H), 8.20(m, 1H), 8.75(m, 1H), 9.04(m, 1H). |
| 15 | NC-[benzene]-N(NHCOCH₂Cl)-CH₂-C(CH₃)₂-O | 150-151 | 2221, 1690 | 1.41(s, 6H), 3.37(s, 2H), 4.16(s, 2H), 6.77-7.20(m, 3H), 8.32(m, 1H). |
| 16 | NC-[benzene]-N(NHCOCH₂OH)-CH₂-C(CH₃)₂-O | 83-85 | 2224, 1685 | 1.40(m, 6H), 3.16, 3.33(sX2, 2H), 4.22(m, 2H), 6.74-7.24(m, 3H), 7.98, 8.70(sX2, 1H). |

TABLE 5

| Comp'd No. | Structural formula | m.p. (°C.) | IR (cm⁻¹) | NMR δ ppm (CDCl₃) |
|---|---|---|---|---|
| 17 | O₂N-[benzene]-N(N(CH₃)COC₂H₅)-CH₂-C(CH₃)₂-O | 124-126 | 1670, 1516, 1337 | 1.14(t, J=7Hz, 3H), 1.46(s, 6H), 2.25(q, J=7Hz, 2H), 3.04(s, 3H), 3.10(d, J=11Hz, 1H), 3.40(d, J=11Hz, 1H), 6.88(d, J=8Hz, 1H), 7.50(d, J=2Hz, 1H), 7.78(dd, J=8.2Hz, 1H). |

TABLE 5-continued

| Comp'd No. | Structural formula | m.p. (°C.) | IR (cm⁻¹) | NMR δ ppm (CDCl₃) |
|---|---|---|---|---|
| 18 | F₃C—[ring]—N(NHCSC₂H₅)—[oxazine with gem-dimethyl] | 108–109 | 3125 1508 | 1.14–1.58(m, 9H), 2.58–2.92(m, 2H), 3.20–3.60(m, 2H), 6.79–7.24(m, 3H), 8.70(m, 1H). |
| 19 | NC—[ring]—N(NHCSC₂H₅)—[oxazine with gem-dimethyl] | 124–125 | 2221 1507 | 1.12–1.60(m, 9H), 2.56–2.90(m, 2H), 3.20–3.60(m, 2H), 6.72–7.30(m, 3H), 8.90(m, 1H). |

TABLE 6

| Comp'd No. | Structural formula | m.p. (°C.) | IR (cm⁻¹) | NMR δ ppm (CDCl₃) |
|---|---|---|---|---|
| 20 | F₃C—[ring]—N(NHCO-3-pyridyl)—[oxazine with gem-dimethyl] | 130–131 | 3232 1665 | 1.43(s, 6H), 3.43(s, 2H), 6.67–7.50(m, 4H), 8.18(m, 1H), 8.70(m, 1H), 8.96–9.18(m, 2H). |
| 21 | O₂N—[ring]—N(NHCO-3-pyridyl)—[oxazine with gem-dimethyl] | 93–95 | 1670 1518 1339 | 1.44(s, 6H), 3.50(s, 2H), 6.84(d, J=8Hz, 1H), 7.32–7.80(m, 3H), 8.22(m, 1H), 8.64–9.20(m, 3H). |
| 22 | O₂N—[ring]—N(NHCOCH₂Br)—[oxazine with gem-dimethyl] | 127–128 | 1684 1521 1338 | 1.38–1.60(m, 6H), 3.30, 3.42(sX2, 2H), 3.90, 3.96(sX2, 2H), 6.85(m, 1H), 7.60–7.90(m, 2H), 8.27(br, 1H). |

TABLE 7

| Comp'd No. | Structural formula | m.p. (°C.) | IR (cm⁻¹) | NMR δ ppm (CDCl₃) |
|---|---|---|---|---|
| 23 | O₂N—[ring]—N(NHCOCH₂ONO₂)—[oxazine with gem-dimethyl] | 150–151 | 1712 1654 1525 1346 | 1.48, 1.52(sX2, 6H), 3.30, 3.38(sX2, 2H), 5.03, 5.16(sX2, 2H), 6.85(m, 1H), 7.55–7.95(m, 3H). |
| 24 | F₃C—[ring]—N(NHCOCH₃)—[oxazine with gem-diethyl] | 139–140 | 3253 1675 1311 | 0.78–1.33(m, 9H), 1.50–1.90(m, 4H), 2.10–2.58(m, 2H), 3.10–3.38(m, 2H), 6.76–7.35(m, 4H). |
| 25 | F₃C—[ring]—N(NHCOC₂H₅)—[oxazine with gem-diethyl] | 120–121 | 3253 1676 1311 | 0.80–1.16(m, 6H), 1.50–1.96(m, 4H), 2.05, 2.10(sX2, 3H), 3.12–3.40(m, 2H), 6.80–7.50(m, 4H). |

TABLE 8

| Comp'd No. | Structural formula | m.p. (°C.) | IR (cm$^{-1}$) | NMR δ ppm (CDCl$_3$) |
|---|---|---|---|---|
| 26 | F$_3$C-phenyl-O-C(C$_2$H$_5$)$_2$-CH$_2$-N(NHCO-3-pyridyl) | 115–116 | 3218<br>1663<br>1314 | 0.96(t, J=8Hz, 6H),<br>1.72(m, 4H), 3.46(s, 2H),<br>6.84–7.60(m, 4H),<br>8.20(m, 1H), 8.52(m, 1H),<br>8.75(m, 1H), 9.06(br, 1H). |
| 27 | F$_5$C$_2$O$_2$S-phenyl-O-C(CH$_3$)$_2$-CH$_2$-N(NHCOCH$_3$) | | 1684<br>1365<br>1134 | 1.30–1.62(m, 6H),<br>2.06, 2.10(sX2, 3H),<br>3.30, 3.42(sX2, 2H),<br>6.95, 7.01(dX2, J=8Hz, 1H),<br>7.24–7.80(m, 3H). |
| 28 | F$_5$C$_2$O$_2$S-phenyl-O-C(CH$_3$)$_2$-CH$_2$-N(NHCOC$_2$H$_5$) | 157–158 | 1665<br>1365<br>1136 | 0.98–1.60(m, 9H),<br>2.05–2.46(m, 2H),<br>3.26, 3.42(sX2, 2H),<br>6.88–7.70(m, 4H). |

TABLE 9

| Comp'd No. | Structural formula | m.p. (°C.) | IR (cm$^{-1}$) | NMR δ ppm (CDCl$_3$) |
|---|---|---|---|---|
| 29 | F$_5$C$_2$O$_2$S-phenyl-O-C(CH$_3$)$_2$-CH$_2$-N(NHCO-3-pyridyl) | 189–190 | 1695<br>1358<br>1126 | 1.49(s, 6H), 3.52(s, 2H),<br>7.01(d, J=8Hz, 1H),<br>7.30–7.65(m, 3H),<br>8.30(m, 1H), 8.74(m, 1H),<br>9.02(m, 1H). |
| 30 | F$_5$C$_2$O$_2$S-phenyl-O-C(CH$_3$)$_2$-CH$_2$-N(NHCO-2-pyridyl) | 166–167 | 1667<br>1360<br>1176 | 1.48(s, 6H), 3.53(s, 2H),<br>7.00(d, J=8Hz, 1H),<br>7.36–7.64(m, 3H),<br>7.80–8.28(m, 2H),<br>8.62(m, 1H), 9.70(s, 1H). |
| 31 | F$_5$C$_2$O$_2$S-phenyl-O-C(CH$_3$)$_2$-CH$_2$-N(NHCO-4-pyridyl) | 160–161 | 1667<br>1360<br>1176 | 1.46(s, 6H),<br>3.52(s, 2H),<br>7.00(d, J=8Hz, 1H),<br>7.22–7.90(m, 4H),<br>8.50–9.05(m, 3H). |

TABLE 10

| Comp'd No. | Structural formula | m.p. (°C.) | IR (cm$^{-1}$) | NMR δ ppm (CDCl$_3$) |
|---|---|---|---|---|
| 32 | 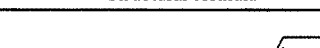 | 105–107 | 2224<br>1684<br>1503 | 1.42(s, 6H), 3.45(s, 2H),<br>6.81(d, J=8Hz, 1H),<br>6.90–7.15(m, 1H),<br>7.81(m, 2H),<br>8.60–9.20(m, 3H). |

TABLE 10-continued

| Comp'd No. | Structural formula | m.p. (°C.) | IR (cm⁻¹) | NMR δ ppm (CDCl₃) |
|---|---|---|---|---|
| 33 | (structure: NC-phenyl-O-C(CH₃)₂-CH₂-N(C₂H₅)(COCH₃)) | 123–124 | 2224, 1666, 1503 | 1.26(t, J=7Hz, 3H), 1.42(s, 3H), 1.45(s, 3H), 2.09(s, 3H), 3.00–3.40(m, 1H), 3.20(d, J=11Hz, 1H), 3.45(d, J=11Hz, 1H), 3.60–4.00(m, 1H), 6.75–6.92(m, 2H), 7.12(dd, J=8.2Hz, 1H). |
| 34 | (structure: F₃C-phenyl-O-cyclopropyl-CH₂-N(NHCOCH₃)) | 169–170 | 1675, 1313, 1121 | 0.60–1.22(m, 4H), 2.04, 2.10(sX2, 3H), 2.80–3.92(m, 2H), 6.68–7.58(m, 4H). |

TABLE 11

| Comp'd No. | Structural formula | m.p. (°C.) | IR (cm⁻¹) | NMR δ ppm (CDCl₃) |
|---|---|---|---|---|
| 35 | (structure: F₃C-phenyl-O-cyclopropyl-CH₂-N(NHCOC₂H₅)) | 206–207 | 1674, 1314, 1123 | 0.60–1.34(m, 7H), 2.08–2.52(m, 2H), 2.80–3.92(m, 2H), 6.68–7.40(m, 4H). |
| 36 | (structure: F₃C-phenyl-O-cyclopropyl-CH₂-N(NHCO-3-pyridyl)) | 116–117 | 1654, 1313, 1123 | 0.68–1.32(m, 4H), 3.62(s, 2H), 6.82(d, J=8Hz, 1H), 6.92–7.20(m, 2H), 7.42(m, 1H), 8.19(m, 1H), 8.60–8.82(m, 2H), 9.06(m, 1H). |
| 37 | (structure: NC-phenyl-O-cyclopropyl-CH₂-N(NHCOCH₃)) | 167–169 | 2228, 1662, 1501 | 0.62–1.30(m, 4H), 2.04, 2.09(sX2, 3H), 2.82–3.96(m, 2H), 6.64–7.22(m, 3H), 7.30, 7.70(sX2, 1H). |

TABLE 12

| Comp'd No. | Structural formula | m.p. (°C.) | IR (cm⁻¹) | NMR δ ppm (CDCl₃) |
|---|---|---|---|---|
| 38 | (structure: NC-phenyl-O-cyclopropyl-CH₂-N(COCH₃)₂) | 150–152 | 2226, 1733, 1506 | 0.68–1.26(m, 4H), 2.43(s, 6H), 3.60(s, 2H), 6.69(d, J=2Hz, 1H), 6.72(d, J=8Hz, 1H), 7.08(dd, J=8.2Hz, 1H). |
| 39 | (structure: NC-phenyl-O-cyclopropyl-CH₂-N(NHCOC₂H₅)) | 143–144 | 2225, 1670, 1505 | 0.62–1.34(m, 7H), 2.08–2.50(m, 2H), 2.80–3.96(m, 2H), 6.66–7.70(m, 4H). |

TABLE 12-continued

| Comp'd No. | Structural formula | m.p. (°C.) | IR (cm⁻¹) | NMR δ ppm (CDCl₃) |
|---|---|---|---|---|
| 40 | 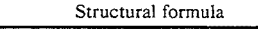 | 182–183 | 2224<br>1733<br>1711 | 0.68–1.24(m, 4H),<br>1.14(t, J=7Hz, 6H),<br>2.78(q, J=7Hz, 4H),<br>3.58(s, 2H),<br>6.64(d, J=2Hz, 1H),<br>6.80(d, J=8Hz, 1H),<br>7.06(dd, J=8.2Hz, 1H). |

TABLE 13

| Comp'd No. | Structural formula | m.p. (°C.) | IR (cm⁻¹) | NMR δ ppm (CDCl₃) |
|---|---|---|---|---|
| 41 | | 126–128 | 2226<br>1651<br>1500 | 0.70–1.22(m, 4H),<br>3.66(s, 2H),<br>6.78(d, J=7Hz, 1H),<br>6.90–7.16(m, 3H),<br>7.50(m, 1H),<br>8.25(m, 1H),<br>8.70(m, 2H). |
| 42 | | | | 8.50–9.20(br, 1H),<br>6.90–7.15(overlapped, 2H),<br>6.80(d, J=8Hz, 1H),<br>3.40(s, 2H),<br>3.35(s, 2H),<br>2.51(s, 3H),<br>1.40(s, 6H). |
| 43 | | Oil | 2223<br>1682<br>1504<br>1270 | 6.90–7.12(overlapped, 2H),<br>6.80(d-like, 1H),<br>3.34(s, 2H),<br>2.96(t-like, 2H),<br>2.50(d, J=7Hz, 2H),<br>2.46(t, J=7Hz, 2H),<br>1.76(qui-like, 1H),<br>1.39(s, 6H),<br>0.93(d, J=7Hz, 6H). |

TABLE 14

| Comp'd No. | Structural formula | m.p. (°C.) | IR (cm⁻) | NMR δ ppm (CDCl₃) |
|---|---|---|---|---|
| 44 | | 163–165 | 2222<br>1679<br>1507<br>1269 | 8.84(br, 1H),<br>7.05(dd, J=1.8, 9Hz, 1H),<br>6.98(d, J=1.8Hz, 1H),<br>6.80(d, J=9Hz, 1H),<br>3.35(s, 2H),<br>3.13(s, 2H),<br>2.37(s, 6H), 1.39(s, 6H). |
| 45 | | 175–178 | 2223<br>1679<br>1506<br>1113 | 8.79(br, 1H),<br>7.04(dd, J=2, 9Hz, 1H),<br>6.92(d, J=2Hz, 1H),<br>6.80(d, J=9Hz, 1H),<br>3.76(m, 4H),<br>3.34(s, 2H), 3.17(s, 2H),<br>2.60(m, 4H), 1.40(s, 6H). |
| 46 | | 207–209 | 1670<br>1361<br>1175 | 7.10–7.50(m, 7H),<br>6.93(d, J=8.5Hz, 1H),<br>3.67(s, 2H),<br>3.39(brs, 2H),<br>1.40(s, 6H). |

TABLE 15

| Comp'd No. | Structural formula | m.p. (°C.) | IR (cm$^{-1}$) | NMR δ ppm (CDCl$_3$) |
|---|---|---|---|---|
| 47 | $C_2F_5SO_2$-[aryl]-N(NHCO-furan)-CH$_2$C(CH$_3$)$_2$-O (benzoxazine) | 206–208 | 1670<br>1360<br>1215<br>1167 | 8.13(brs, 1H),<br>7.54(d, J=1.5Hz, 1H),<br>7.45(dd, J=2, 8.5Hz, 1H),<br>7.41(d, J=2Hz, 1H),<br>7.25(d, J=3.5Hz, 1H),<br>7.00(d, J=8.5Hz, 1H),<br>6.59(dd, J=1.5, 3.5Hz, 1H),<br>3.52(brs, 2H), 1.48(s, 6H). |
| 48 | $C_4F_9SO_2$-[aryl]-N(NHCOCH$_3$)-CH$_2$C(CH$_3$)$_2$-O | Oil | 1684<br>1367<br>1169 | 8.17, 8.13(brsX2, 1H),<br>7.20–7.62(m, 1H),<br>7.01, 6.95(dX2, J=9Hz, 1H),<br>3.37, 3.30(sX2, 2H),<br>2.09, 2.02(sX2, 3H),<br>1.51, 1.47, 1.40(sX3, 6H). |
| 49 | $C_4F_9SO_2$-[aryl]-N(NHCOC$_2$H$_5$)-CH$_2$C(CH$_3$)$_2$-O | 104–106 | 1667<br>1365<br>1169 | 7.18–7.78(m, 2H),<br>7.00, 6.94(dX2, J=9Hz, 1H),<br>3.41, 3.27(sX2, 2H),<br>2.00–2.52(m, 2H),<br>1.50, 1.47, 1.41(sX3, 6H),<br>1.20(t, J=7Hz, 3H). |

TABLE 16

| Comp'd No. | Structural formula | m.p. (°C.) | IR (cm$^{-1}$) | NMR δ ppm (CDCl$_3$) |
|---|---|---|---|---|
| 50 | $C_4F_9SO_2$-[aryl]-N(NHCO-3-pyridyl)-CH$_2$C(CH$_3$)$_2$-O | 80–83 | 1670<br>1364<br>1168 | 9.60(s, 1H),<br>9.06(brs, 1H),<br>8.70(brd, 1H),<br>8.19(brd, J=9Hz, 1H),<br>7.20–7.53(m, 2H),<br>6.97(d, J=9Hz, 1H),<br>3.51(s, 2H), 1.45(s, 6H). |
| 51 | $C_4F_9SO_2$-[aryl]-N(NHCO-C$_6$H$_4$-CN)-CH$_2$C(CH$_3$)$_2$-O | 110–112 | 2234<br>1674<br>1369<br>1168 | 8.54(brs, 1H),<br>7.28–8.24(m, 6H),<br>7.00(d, J=9Hz, 1H),<br>3.50(brs, 2H),<br>1.45(s, 6H). |
| 52 | $C_4F_9SO_2$-[aryl]-N(NHCO-C$_6$H$_4$-NO$_2$)-CH$_2$C(CH$_3$)$_2$-O | 180–182 | 1698<br>1352<br>1137 | 8.30(m, 3H),<br>7.97(d, J=9Hz, 2H),<br>7.37(m, 2H),<br>7.00(d, J=8Hz, 1H),<br>3.54(brs, 2H),<br>1.47(s, 6H). |

TABLE 17

| Comp'd No. | Structural formula | m.p. (°C.) | IR (cm$^{-1}$) | NMR δ ppm (CDCl$_3$) |
|---|---|---|---|---|
| 53 | $C_4F_9SO_2$-[aryl]-N(NHCOOCH$_3$)-CH$_2$C(CH$_3$)$_2$-O | Oil | 1728<br>1367 | 7.40(m, 2H),<br>6.94(overlapped, 2H),<br>3.72(s, 3H),<br>3.35(brs, 2H),<br>1.43(s, 6H). |
| 54 | $C_4F_9SO_2$-[aryl]-N(NHCOOC$_6$H$_5$)-CH$_2$C(CH$_3$)$_2$-O | 111–114 | 1737<br>1364<br>1184 | 6.80–7.60(m, 9H),<br>3.44(brs, 2H),<br>1.44(s, 6H). |

TABLE 17-continued

| Comp'd No. | Structural formula | m.p. (°C.) | IR (cm$^{-1}$) | NMR δ ppm (CDCl$_3$) |
|---|---|---|---|---|
| 55 | C$_4$F$_9$SO$_2$—[benzoxazine with NHCO-CH=CH-C$_6$H$_5$ substituent and gem-dimethyl] | 161–163 | 1668<br>1363<br>1174 | 6.70–7.85(m, 9H),<br>6.50(d, J=15Hz, 1H),<br>3.46(brs, 2H), 1.44(s, 6H). |

TABLE 18

| Comp'd No. | Structural formula | m.p. (°C.) | IR (cm$^{-1}$) | NMR δ ppm (CDCl$_3$) |
|---|---|---|---|---|
| 56 | CF$_3$SO$_2$—[benzoxazine, NHCOCH$_3$] | 128–130 | 1679<br>1362<br>1211 | 1.30–1.60(m, 6H),<br>2.08, 2.11(sX2, 3H),<br>3.29, 3.42(sX2, 2H),<br>6.96, 7.02(dX2, J=8Hz, 1H),<br>7.24–7.72(m, 3H). |
| 57 | CF$_3$SO$_2$—[benzoxazine, NHCOC$_2$H$_5$] | 203–205 | 1668<br>1360<br>1213 | 1.00–1.56(m, 9H),<br>2.10–2.50(m, 2H),<br>3.26, 3.42(sX2, 2H),<br>6.86–7.60(m, 4H). |
| 58 | CF$_3$SO$_2$—[benzoxazine, NHCO-(3-pyridyl)] | 195–196 | 1661<br>1360<br>1204 | 1.48(s, 6H),<br>3.54(s, 2H),<br>7.00(d, J=8Hz, 1H),<br>7.25–7.54(m, 3H),<br>8.18(m, 1H),<br>8.62–8.92(m, 2H),<br>9.03(m, 1H). |

We claim:

1. A 1,4-benzoxazine derivative represented by the following formula (1):

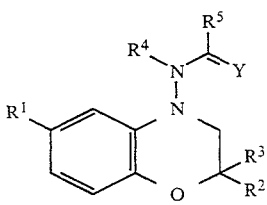

(1)

wherein:

R$^1$ represents a halogenated lower alkyl, a halogenated lower alkylsulfonyl, nitro or cyano group, R$^2$ and R$^3$ may be the same or different and individually represent a hydrogen atom or a lower alkyl group or are fused together with the adjacent carbon atom into a 3- to 6-membered carbon ring, R$^4$ represents a hydrogen atom, a lower alkyl group or a lower alkanoyl group, R$^5$ represents a hydrogen atom; a lower alkyl group; a lower alkyl group substituted by hydroxy, nitroxy, phenyl, lower alkyl amino or morpholino; a lower alkenyl group; a lower alkenyl group substituted by phenyl; a lower alkoxy group; a phenyl group; a phenyl group substituted by halogen, aminosulfonyl, nitro or cyano; a naphthyl group; a phenoxy group; a pyrrolyl group; an oxazyl group; an imidazolyl group; a pyridyl group; a pyrimidyl group; a furanyl group; or a thienyl group; and Y represents an oxygen or sulfur atom.

2. The 1,4-benzoxazine derivative of claim 1 wherein R$^1$ is a cyano group.

3. The 1,4-benzoxazine derivative of claim 2 wherein R$^2$ and R$^3$ are each methyl groups, R$^4$ is hydrogen, R$^5$ is ethyl, and Y is oxygen.

4. The 1,4-benzoxazine derivative of claim 2 wherein R$^2$ and R$^3$ are each methyl groups, R$^4$ is hydrogen, R$^5$ is 3-pyridinyl, and Y is oxygen.

5. The 1,4-benzoxazine derivative of claim 1 wherein R$^1$ is a nitro group.

6. The 1,4-benzoxazine derivative of claim 5 wherein R$^2$ and R$^3$ are each methyl groups, R$^4$ is hydrogen, R$^5$ is an ethyl group, and Y is oxygen.

7. The 1,4-benzoxazine derivative of claim 5 wherein R$^2$ and R$^3$ are each methyl groups, R$^4$ is hydrogen, R$^5$ is a vinyl group, and Y is oxygen.

8. The 1,4-benzoxazine derivative of claim 1 wherein R$^1$ is a halogenated lower alkyl group.

9. The 1,4-benzoxazine derivative of claim 8 wherein R$^1$ is a trifluoromethyl group, R$^2$ and R$^3$ are each methyl groups, R$^4$ is hydrogen, R$^5$ is a 3-pyridinyl group, and Y is oxygen.

10. The 1,4-benzoxazine derivative of claim 8 wherein R$^1$ is a trifluoromethyl group, R$^2$ and R$^3$ are each ethyl groups, R$^4$ is hydrogen, R$^5$ is a methyl group, and Y is oxygen.

11. The 1,4-benzoxazine derivative of claim 1 wherein R$^1$ is a halogenated lower alkylsulfonyl group.

12. The 1,4-benzoxazine derivative of claim 11 wherein R$^1$ is a perfluoroethylsulfonyl group, R$^2$ and R$^3$ are each methyl groups, R$^4$ is hydrogen, R$^5$ is a methyl group, and Y is oxygen.

13. The 1,4-benzoxazine derivative of claim 11 wherein $R^1$ is a trifluoromethylsulfonyl group, $R^2$ and $R^3$ are each methyl groups, $R^4$ is hydrogen, $R^5$ is a methyl group and Y is oxygen.

14. The 1,4-benzoxazine derivative of claim 11 wherein $R^1$ is a trifluoromethylsulfonyl group, $R^2$ and $R^3$ are each methyl groups, $R^4$ is hydrogen, $R^5$ is an ethyl group and Y is oxygen.

15. The 1,4-benzoxazine derivative of claim 11 wherein $R^1$ is a trifluoromethylsulfonyl group, $R^2$ and $R^3$ are each methyl groups, $R^4$ is hydrogen, $R^5$ is a 3-pyridinyl group, and Y is oxygen.

* * * * *